United States Patent [19]

Nowakowski et al.

[11] Patent Number: 4,945,113
[45] Date of Patent: Jul. 31, 1990

[54] HERBICIDAL SULFONAMIDE DERIVATIVES

[75] Inventors: Mark A. Nowakowski, Haddam; Allyn R. Bell, Cheshire, both of Conn.

[73] Assignee: Uniroyal Chemical Company, Inc., Middlebury, Conn.

[21] Appl. No.: 414,977

[22] Filed: Sep. 29, 1989

[51] Int. Cl.$^5$ .................................... A01N 41/06
[52] U.S. Cl. ...................................... 514/605; 564/99
[58] Field of Search ........................ 564/99; 514/605

[56] References Cited

U.S. PATENT DOCUMENTS

| | | | |
|---|---|---|---|
| 4,452,629 | 6/1984 | Heiba | 71/103 |
| 4,465,508 | 8/1984 | Barton | 71/103 |
| 4,744,812 | 5/1988 | Parg | 71/88 |
| 4,744,818 | 5/1988 | Heiba | 71/94 |

OTHER PUBLICATIONS

Chemical Abstracts 101;191337b, p. 714 (1984).
Chemical Abstracts 101:90771h, pp. 626–627 (1984).
Chemical Abstracts 102:166479n, p. 592 (1985).
Chemical Abstracts 102:13174h, p. 598 (1985).
Chemical Abstracts 102:61941d, p. 570 (1985).

Primary Examiner—Richard L. Raymond
Assistant Examiner—Scott C. Rand
Attorney, Agent, or Firm—Glenn E. Karta

[57] ABSTRACT

Compounds having the structure

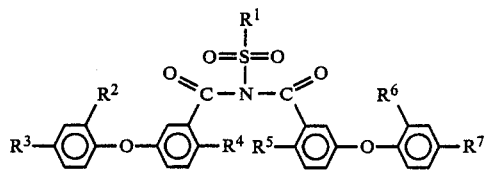

wherein:
$R^1$ is $C_1$-$C_8$ alkyl;
$R^2$, $R^3$, $R^6$ and $R^7$ are each independently halogen or trihalomethyl; and
$R^4$ and $R^5$ are halogen, cyano or nitro;

are disclosed which have herbicidal activity. Herbicidal compositions comprising the compounds and a carrier are also disclosed, as are methods for controlling the growth of undesirable plants utilizing the compounds. Methods for the preparation of such compounds are also disclosed.

8 Claims, No Drawings

HERBICIDAL SULFONAMIDE DERIVATIVES

BACKGROUND OF THE INVENTION

1. Field of the Invention

This invention relates to a class of sulfonamide derivatives having substituted thereon an (optionally substituted) phenoxybenzoate moiety, which compounds exhibit unexpectedly desirable pre- and post-emergent herbicidal activity. In other aspects, this invention relates to a herbicidal composition comprising such novel compounds as well as to a method of controlling the growth of undesirable plants, such as weeds, employing the novel herbicides of this invention. In yet another aspect, this invention relates to a process for producing such compounds.

Weeds compete with crops for light, moisture, nutrients and space. Thus, weeds inhibit the production of foliage, fruit or seed of agricultural crops. The presence of weeds may also reduce the quality of the harvested crop and reduce harvesting efficiency. Weed control is essential for maximum production of many agronomic and horticultural crops including corn, (*Zea mays* L.), cotton (*Gossypium SP*), sunflower (*Hellianthus annus* L.) and soybeans (*Glycine max* (L.) Merr.). Weeds on noncropped areas may cause a fire hazard, undesirable drifting of sand or snow, or irritation to persons with allergies. Thus, suppression of undesirable weed growth is very advantageous.

While a large number of compounds possessing herbicidal activity are known, it would be nonetheless desirable to possess additional compounds which would effectively control the growth of unwanted vegetation.

2. Description of Related Art

U.S. Pat. No. 4,465,508 discloses certain substituted diphenyl ethers useful as herbicides. Somewhat similar herbicidal substituted diphenyl ethers are disclosed in Chemical Abstracts 102:131714h (1985); 102:166479n (1985); 102:61941d (1985); 101:191337b (1984); 101:90771h (1984); and U.S. Pat. Nos. 4,744,812 and 4,744,818. Finally, U.S. Pat. No. 4,452,629 discloses certain N,N'(thio)-5(substituted-phenoxy or pyridyloxy)-2-substituted benzoic acid sulfonamides and sulfamidoyl fluoride derivatives which exhibit herbicidal activity.

However, the compounds disclosed in the above references differ significantly in structure from the N,N-bis [benzyl-phenoxy] sulfonamides of the present invention.

SUMMARY OF THE INVENTION

In one aspect, this invention relates to a compound of the formula:

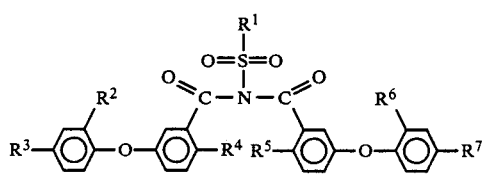

wherein:
$R^1$ is $C_1$-$C_8$ alkyl;
$R^2$, $R^3$, $R^6$ and $R^7$ are each independently halogen or trihalomethyl; and
$R^4$ and $R^5$ are halogen, cyano or nitro.

In another aspect, this invention relates to a herbicidal composition comprising:

(A) a compound having the structure of formula (I) above; and (B) a suitable carrier.

In yet another aspect, this invention relates to a method of controlling the growth of undesirable plants, which method comprises applying a herbicidally effective amount of a composition comprised of:

(A) a compound having a structure in accordance with formula (I), and (B) a suitable carrier.

In a further aspect, this invention relates to a process for preparing a compound having the structure of formula (I) wherein a substituted benzoyl alkane sulfonamide is reacted with a phenoxybenzoylhalide in the presence of potassium tertiary butoxide.

DESCRIPTION OF THE PREFERRED EMBODIMENTS

The compounds of this invention have the structural formula

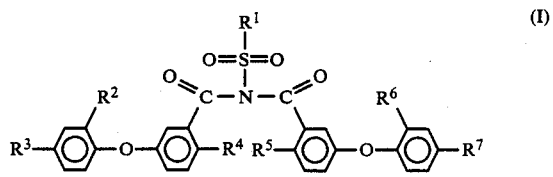

wherein:
$R^1$ is $C_1$-$C_8$ alkyl;
$R^2$, $R^3$, $R^6$ and $R^7$ are each independently halogen or trihalomethyl; and
$R^4$ and $R^5$ are halogen, cyano or nitro.

A preferred compound has structure I above wherein $R^1$ is methyl; $R^2$ and $R^6$ are chloro; $R^3$ and $R^7$ are $CF_3$ and $R^4$ and $R^5$ are nitro.

The compounds of this invention are prepared by reacting a substituted benzoyl alkane sulfonamide of the formula:

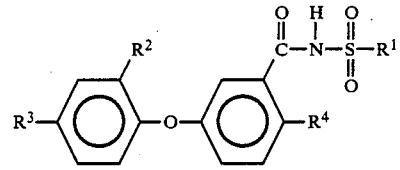

with a phenoxybenzoylhalide of the formula:

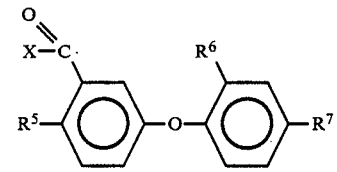

in the presence of potassium tertiary butoxide wherein $R^1$, $R^2$, $R^3$, $R^4$, $R^5$, $R^6$ and $R^7$ are as defined in formula (I) above; and wherein X is halogen, preferably chlorine. The substituted benzoyl alkane sulfonamide intermediates may be readily prepared by reacting the suitably substituted phenoxybenzoylhalide with methane sulfonamide. The phenoxybenzoylhalide may be prepared by the reaction of the suitably substituted phenoxybenzoic acid with thionyl chloride.

The substituted benzoyl alkane sulfonamide and substituted phenoxybenzoylhalide reactants are reacted in the presence of potassium tertiary butoxide in order to produce the final compounds. This reaction is typically conducted in a nonreactive organic solvent such as tetrahydrofuran. The reactants are preferably employed in about equimolar ratios, generally of between about 1.25:1 and 1:1.25 moles of benzamide to moles of phenoxybenzoylhalide.

The crude reaction product so produced is then typically isolated from the reaction medium by first being diluted with toluene, washed with water and saturated sodium chloride solution. The organic phase is then concentrated by vacuum to dryness. The residue may be further purified by conventional means, such as by column chromatography or by recrystallization from toluene/hexane mixtures.

The compositions of this invention are comprised of (a) an herbicidally effective amount of at least one compound having a structure in accordance with formula (I) as the active ingredient(s), and (b) a suitable carrier.

To prepare such agriculturally useful compositions, the active ingredient(s) may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the agriculturally active compound may be impregnated on finely-divided or granular inorganic or organic carriers such as appapulgite clay, sand, vermiculite, corn cob, activated carbon or other granular carriers known to the art. The impregnated granules may then be spread on the soil or incorporated into the soil.

Alternatively, the active ingredient(s) may be formulated as a wettable powder by grinding it into a fine powder and mixing it with an inactive powdered carrier to which a surface active dispersing agent has been added. Typical powdered solid carriers are the various mineral silicates (such as mica, talc, pyrophyllite, clays and the like) or powdered organic materials (e.g., corn cob). The wettable powder may then be dispersed in water and sprayed on the soil surface, or on crop or weed plants.

Similarly, an emulsifiable concentrate may be prepared by dissolving the active ingredient(s) in a solvent such as benzene, toluene, or other aromatic or aliphatic hydrocarbon to which a surface active dispersing agent generally has been added. The emulsifiable concentrate may then be dispersed in water and applied by spraying.

The concentration of active ingredient(s) in the composition may vary widely, typically ranging from about 1% to about 95% by weight. The concentration of active ingredient(s) in dispersions applied to the soil of foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulation may be applied to the soil either as a liquid or a granule.

For use as a preemergence herbicide, the compound of this invention is typically applied at a rate from about 0.05 to about 25 pounds per acre (about 0.056 to about 28 kg/ha) to soil which contains weed and crop seed. Such application is made either to the surface of the soil or into the upper one to three inches (2.5 to 7.5 cm.) of soil. When employed as a postemergence herbicide the compound is typically applied at a rate of from about 0.05 to about 25 pounds per acre (about 0.056 to about 28 kg/ha) to the aerial portions of weeds.

The most suitable rate of application in any given case may depend on such factors as soil type, soil pH, soil organic matter content, the quantity and intensity of rainfall before and after treatment, the air and soil temperature, light intensity and light duration per day. All of these factors can have an influence on the efficacy of the chemicals for a given weed control use. However, one skilled in the art can, by routine experimentation, readily determine optimum conditions for employment of any particular diphenyl ether compound.

The herbicidal use may include control of vegetation at industrial sites or selective weed control in crop fields.

EXAMPLES

The following Examples are intended to further illustrate the invention and are not intended to limit the scope of the invention in any manner whatsoever.

EXAMPLE 1

Preparation of
5-[2-chloro-4-(trifluoromethyl)phenoxy]-2-nitrobenzoyl chloride 108.4 grams of 5-[2-chloro-4-(trifluoromethyl)-phenoxy-2-nitrobenzoic acid were refluxed in 100 ml of thionyl chloride for thirty minutes. The volatiles were then stripped off under vacuum (15 mm Hg, 60° C.) and the residue redissolved in toluene and reconcentrated twice more to remove all traces of volatiles. The resulting product, 5-[2-chloro-4-(trifluoromethyl)phenoxy]-2-nitrobenzoyl chloride, 108.5 grams, was not purified any further.

EXAMPLE 2

Preparation of intermediate
N-methylsulfonyl-5]-2-chloro-4-(trifluoromethyl)-phenoxy]-2-nitrobenzamide Methane sulfonamide was added to 5-[2-chloro-4-(trifluoromethyl)phenoxy]-2-nitrobenzoyl chloride, and the mixture was covered with dry toluene. The mixture was stirred in an ice bath and dry pyridine was added. The ice bath was then removed, and the mixture was heated to reflux for two hours. The mixture was then cooled, washed three times each with water, 1% HCl, saturated $NaHCO_3$ and water again, dried over $MgSO_4$ then filtered and dried to yield the desired amide product. The amide has a melting point of 197°–198.5° C.

EXAMPLE 3

Preparation of N,N-bis[5-(2-chloro-4-(trifluoromethyl)phenoxy)-2-nitrobenzoyl]methane sulfonamide (Compound 1)

To N-methylsulfonyl-5-[2-chloro-4-(trifluoromethyl)phenoxy]-2-nitro-benzamide (20.0 grams, 45.6 millimoles) dissolved in 100 ml tetrahydrofuran was added potassium tertiary butoxide in tetrahydrofuran with cooling. A solution of the acid chloride product as described in Example 1 in tetrahydrofuran was then added and the mixture stirred at ambient temperature for forty eight hours under nitrogen with precautions taken to exclude moisture throughout this procedure. The mixture was then diluted with toluene, washed three times with water and saturated sodium chloride solution. The organic phase was concentrated by vacuum to dryness. The residue was shaken with toluene then reconcentrated three times. The final residue was covered with toluene, shaken, the insolubles filtered off, and washed several more times with toluene and hexane. The material was triturated for 30 minutes by stirring with 50 ml hexane. The insolubles were filtered off and dried. The material was purified further by trituration with 5% potassium carbonate followed by drying and recrystallization from toluene/hexane mixtures. The desired product had a melting point of 165.5°–167.5° C.

The product had a structure of Formula I above wherein $R^1$ is $CH_3$; $R^2$ and $R^6$ are Cl; $R^3$ and $R^7$ are $CF_3$ and $R^4$ and $R^5$ are $NO_2$. The structure was confirmed by NMR spectra.

EXAMPLE 4

Preemergence Control

To illustrate the effectiveness of the compounds of this invention as preemergence herbicides, 300 mg of N,N-bis[5-(2-chloro-4-(trifluoromethyl)phenoxy-2-nitrobenzoyl] methane sulfonamide (compound 1) were dissolved in 10 ml acetone to which 30 mg of an emulsifying agent, ethoxylated sorbitan monolaurate, were added. The solution was diluted to 100 ml with distilled water. Ten milliliters of the 3000 ppm solution were diluted to 250 ppm with distilled water. The chemical was applied at the rate of 10 lb/A (11.2 kg/ha) by drenching 46 ml of the 250 ppm solution on the surface of soil in 4½ inch (11.25 cm) plastic pots wherein seeds of the following weeds had been planted: Prickly sida (*Sida spinosa* L.) (PS), jimsonweed (*Datura stramonium* L. (JW), tall morning glory (*Ipomea purpurea* L. Roth) (TM), wild oats (*Avena fatua* L.) (WO), barnyardgrass (*Echinochloa crusgalli* L. Beauv.) (BG), and green foxtail (*Setaria viridis* (L.), Beauv.) (GF). Application at 1 lb/A (1.12 kg/ha) was accomplished by dilution of the test solution to 25 ppm and drenching 46 ml onto each pot surface as described previously. The percent control of the weeds compared to untreated checks was determined two weeks after treatment. The results of such testing are summarized in Table I. The data presented in such table indicates the good to excellent herbicidal efficacy.

TABLE I

| Rate lb/A | Preemergence Activity Greenhouse Data Percent Weed Control | | | | | |
|---|---|---|---|---|---|---|
| | JW | PS | TM | WO | GF | BG |
| 10 | 100 | 100 | 100 | 95 | 100 | 100 |
| 1 | 90 | 95 | 50 | 30 | 100 | 85 |

EXAMPLE 5

Postemergence Control

To test the effectiveness of the compounds of this invention as postemergence herbicides, a 3000 ppm solution of compound 1 (produced in accordance with the process described in Example 4) was atomized employing a DeVILBISS [trademark] sprayer, wetting the foliage to the drip point. The remainder of the procedure was the same as described under Example 4. The weeds, which were the same species as described under Example 4, were treated six days after emergence. The percent weed control was evaluated two weeks after treatment. The results of such testing are summarized in Table II.

TABLE II

| Rate PPM | Postemergence Activity Greenhouse Data Percent Weed Control | | | | | |
|---|---|---|---|---|---|---|
| | JW | PS | TM | WO | GF | BG |
| 3000 | 100 | 98 | 100 | 60 | 100 | 100 |
| 500 | 100 | 98 | 100 | 40 | 85 | 60 |

EXAMPLE 6

Three field tests were run which compared compound 1 of the present invention with a commercial formulation of the sodium salt of 5-[2-chloro-4-(triflouromethyl)]phenoxy-2-nitrobenzoic acid, a known herbicidal compound which was sold commercially by Rohm & Haas under the mark BLAZER. A formulation was made containing 11% compound 1, 79% isophorone (solvent) and 10% Sponto N193 BU (surfactant) resulting in one pound of active ingredient per gallon of formulation. This formulation was dispersed in water at the rates of 1 quart or 2 quarts per 30 gallons of final spray solution to give ¼ lb or ½ lb of active ingredient per acre. Table III presents data from three separate field tests treated as described.

TABLE III

| | | Postemergence Activity Field Data (1) Percent Weed Control | | | | |
|---|---|---|---|---|---|---|
| Cpd. | Rate lb/A | Morning Glory | Velvet Leaf | Pig Weed | Giant Foxtail | Soy Bean |
| 1. | 1/4 | 96 | 98 | 100 | 25 | 20 |
| BLAZER | 1/2 | 100 | 92 | 100 | 22 | 23 |

| | | Percent Weed Control | | | | |
|---|---|---|---|---|---|---|
| Cpd. | Rate lb/A | Morning Glory | Velvet Leaf | Pig Weed | Green Foxtail | Yellow Foxtail | Soy Bean |

TABLE III-continued

| | | | Postemergence Activity | | | | |
|---|---|---|---|---|---|---|---|
| | | | Field Data (2) | | | | |
| 1. | 1/2 | 95 | 97 | 100 | 40 | 63 | 0 |
| 1. | 1/4 | 90 | 87 | 97 | 13 | 37 | 0 |
| BLAZER | 1/2 | 93 | 90 | 98 | 67 | 73 | 0 |
| | | | Field Data (3) | | | | |
| 1. | 1/2 | 93 | 43 | 33 | 70 | 70 | 0 |
| 1. | 1/4 | 83 | 30 | 30 | 23 | 13 | 0 |
| BLAZER | 1/2 | 93 | 37 | 27 | 83 | 90 | 0 |

We claim:

1. A compound having the structural formula:

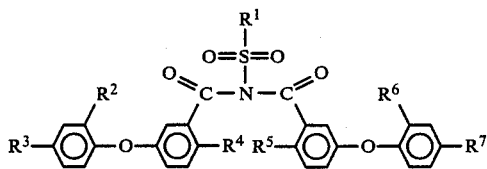

wherein $R^1$ is $C_1$–$C_8$ alkyl; $R^2$, $R^3$, $R^6$ and $R^7$ are each independently halogen or tri-halomethyl; and $R^4$ and $R^5$ are halogen, cyano or nitro.

2. A compound in accordance with claim 1 wherein $R^1$ is methyl; $R^2$ and $R^6$ are chloro; $R^4$ and $R^5$ are $CF_3$ and $R^4$ and $R^5$ are nitro.

3. An herbicidal composition comprising
(A) a compound having the structural formula:

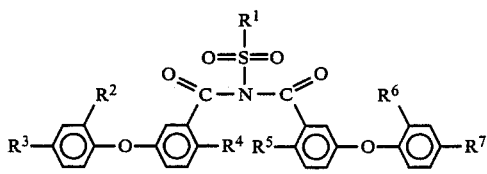

wherein $R^1$ is $C_1$–$C_8$ alkyl; $R^2$, $R^3$, $R^6$ and $R^7$ are each independently halogen or tri-halomethyl; and $R^4$ and $R^5$ are halogen, cyano or nitro; and
(B) a suitable carrier.

4. A composition in accordance with claim 3 wherein in component (A): $R^1$ is methyl; $R^2$ and $R^6$ are chloro; $R^3$ and $R^7$ are $CF_3$ and $R^4$ and $R^5$ are nitro.

5. A method for controlling the growth of undesirable plants comprising applying to the locus of such plants an herbicidally effective amount of a compound having the structural formula:

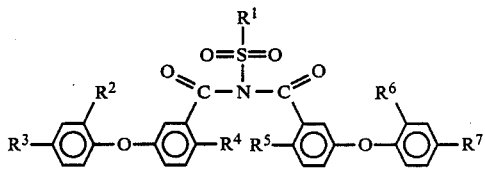

wherein $R^1$ is $C_1$–$C_8$ alkyl; $R^2$, $R^3$, $R^6$ and $R^7$ are each independently halogen or tri-halomethyl; and $R^4$ and $R^5$ are halogen, cyano or nitro.

6. A method in accordance with claim 5 wherein $R^1$ is methyl; $R^2$ and $R^6$ are chloro; $R^3$ and $R^7$ are $CF_3$ and $R^4$ and $R^5$ are nitro.

7. A method in accordance with claim 5 wherein the compound is applied pre-emergently.

8. A method in accordance with claim 5 wherein the compound is applied post-emergently.

* * * * *